United States Patent
Hagg et al.

(10) Patent No.: US 11,801,246 B2
(45) Date of Patent: Oct. 31, 2023

(54) METHODS OF TREATING ISCHEMIC DISEASE BY ADMINISTERING AN ATR KINASE INHIBITOR

(71) Applicant: East Tennessee State University Research Foundation, Johnson City, TN (US)

(72) Inventors: Theodoor Hagg, Johnson City, TN (US); Yue Zou, Johnson City, TN (US)

(73) Assignee: EAST TENNESSEE STATE UNIVERSITY RESEARCH FOUNDATIO, Johnson City, TN (US)

( * ) Notice: Subject to any disclaimer, the term of this patent is extended or adjusted under 35 U.S.C. 154(b) by 461 days.

(21) Appl. No.: 16/677,945

(22) Filed: Nov. 8, 2019

(65) Prior Publication Data

US 2020/0147077 A1    May 14, 2020

Related U.S. Application Data

(60) Provisional application No. 62/758,126, filed on Nov. 9, 2018.

(51) Int. Cl.
| | | |
|---|---|---|
| *A61K 31/497* | (2006.01) | |
| *A61P 25/28* | (2006.01) | |
| *A61K 38/48* | (2006.01) | |
| *A61K 45/06* | (2006.01) | |

(52) U.S. Cl.
CPC .......... *A61K 31/497* (2013.01); *A61K 38/482* (2013.01); *A61P 25/28* (2018.01); *A61K 45/06* (2013.01); *C12Y 304/21068* (2013.01)

(58) Field of Classification Search
CPC .... A61K 31/497; A61K 38/482; A61K 45/06; A61P 25/28; C12Y 304/21068
See application file for complete search history.

(56) References Cited

U.S. PATENT DOCUMENTS

2014/0356456 A1  12/2014 Pollard et al.
2019/0008856 A1*  1/2019 Lord ..................... A61K 31/497

OTHER PUBLICATIONS

Fujiwara N, Murata Y, Arai K, Egi Y, Lu J, Wu O, Singhal AB, Lo EH. Combination therapy with normobaric oxygen (NBO) plus thrombolysis in experimental ischemic stroke. BMC Neurosci. Jul. 15, 2009;10:79. doi: 10.1186/1471-2202-10-79. PMID: 19604385; PMCID: PMC2714858. (Year: 2009).*
Dong Y, Benveniste EN. Immune function of astrocytes. Glia. Nov. 2001;36(2):180-90. doi: 10.1002/glia.1107. PMID: 11596126. (Year: 2001).*
Ahn, Kee-Chan; MacKenzie, Erin M.; Learman, Cameron R.; Hall, Tia C.; Weaver, Charles L.; Dunbar, Gary L.; Song, Mee-Sook Inhibition of p53 attenuates ischemic stress-induced activation of astrocytes, NeuroReport: Sep. 30, 2015—vol. 26—Issue 14:p. 862-869 doi: 10.1097/WNR.0000000000000439 (Year: 2015).*
Xing C, Arai K, Lo EH, Hommel M. Pathophysiologic cascades in ischemic stroke. Int J Stroke. 2012;7(5):378-385. doi:10.1111/j.1747-4949.2012.00839.x (Year: 2012).*
Bieging KT, Mello SS, Attardi LD. Unravelling mechanisms of p53-mediated tumour suppression. Nat Rev Cancer. May 2014;14(5):359-70. doi: 10.1038/nrc3711. Epub Apr. 17, 2014. PMID: 24739573; PMCID: PMC4049238. (Year: 2014).*
Palwinder K. Mander, Aiste Jekabsone, Guy C. Brown. Microglia Proliferation Is REgulated by Hydrogen Peroxide from NADPH Oxidase. The Journal of Immunology Jan. 15, 2006, 176 (2) 1046-1052; DOI: 10.4049/jimmunol.176.2.1046 (Year: 2006).*
Ischemia, Wikipedia. Retrieved on the Wayback Machine on May 16, 2022, https://web.archive.org/web/20190911051101/https://en.wikipedia.org/wiki/Ischemia. Published Sep. 11, 2019. (Year: 2019).*
Hulme A, MacLennan WJ, Ritchie RT, John VA, Shotton PA. Baclofen in the elderly stroke patient its side-effects and pharmacokinetics. Eur J Clin Pharmacol. 1985;29(4):467-9. (Year: 1985).*
Teasell, Robert W et al. "A systematic review of pharmacologic treatments of pain after spinal cord injury." Archives of physical medicine and rehabilitation vol. 91,5 (2010): 816-31. doi:10.1016/j.apmr.2010.01.022 (Year: 2010).*
Cristobal et al. "Pharmacological modulation of retinal ischemia—reperfusion syndrome in rates." ARVO Annual Meeting Abstract, Investigative Ophthalmology & Visual Science, vol. 59, 5287. Jul. 2018. (Year: 2018).*
Chujo K, Ueki M, Asaga T, Taie S. Atrial natriuretic peptide attenuates ischemia/reperfusion-induced renal injury by reducing neutrophil activation in rats. Tohoku J Exp Med. Jul. 2008;215(3):257-66. (Year: 2008).*
Charrier, et al., Discovery of Potent and Selective Inhibitors of Ataxia Telangiectasia and Rad3 Related (ATR) Protein Kinase as Potential Anticancer Agents, J. Med. Chem. 54(7): 2320-30 (2011).
Foote, et al., Discovery and Characterization of AZD6738, a Potent Inhibitor of Ataxia Telangiectasia Mutated and RAD3 Related (ATR) Kinase with Application as an Anticancer Agent, J. Med. Chem. 61(22): 9889-9907 (2018).
Kalogeris, et al., Cell Biology of Ischemia/Reperfusion Injury, Int. Rev. Cell Mol. Biol. 298: 229-317 (2012).
Kang, et al., Loss of neuron-astroglia interaction rapidly induces protective CNTF expression after stroke in mice, J. Neuroscience 32: 9277-87 (2012).
Kang et al., Endogenous CNTF mediates stroke-induced adult CNS neurogenesis in mice, Neurobiology of Disease 49: 68-78 (2013).

(Continued)

*Primary Examiner* — Brandon J Fetterolf
*Assistant Examiner* — Lauren Wells
(74) *Attorney, Agent, or Firm* — DINSMORE AND SHOHL, LLP (57) ABSTRACT

A method of treating a subject suffering from an ischemic disease associated with $Ca^{2+}$ overload is provided, the method including administering to the subject an effective amount of an inhibitor of *Ataxia telangiectasia* and Rad3-related (ATR) kinase. Also provided is a method of treating a subject suffering from acute ischemic stroke, the method including administering to the subject an effective amount of the ATR kinase inhibitor berzosertib.

22 Claims, 8 Drawing Sheets
(3 of 8 Drawing Sheet(s) Filed in Color)

(56) References Cited

OTHER PUBLICATIONS

Knegtel, et al., Rational Design of 5-(4-(Isopropylsulfonyl)phenyl)-3-(3-(4-((methylamino)methyl)phenyl)isoxazol-5-yl) pyrazine-2-amine (VX-970, M6620): Optimization of Intra- and Intermolecular Polar Interactions of a New Ataxia Telangiectasia Mutated and Rad3-Related (ATR) Kinase Inhibitor, J. Med. Chem. 62(11): 5547-61 (2019).

Krysko et al., Apoptosis and necrosis: detection, discrimination and phagocytosis, Methods 44(3): 205-21 (2008).

Mei, et al., Ataxia telangiectasia and Rad3-related inhibitors and cancer therapy: where we stand, J. Hematol. Oncol. 12: 43 (2019).

Vandenabeele et al., Molecular mechanisms of necroptosis: an ordered cellular explosion, Nat. Rev. Mol. Cell Biol. 11: 700-14 (2010).

* cited by examiner

METHODS OF TREATING ISCHEMIC DISEASE BY ADMINISTERING AN ATR KINASE INHIBITOR

CROSS REFERENCE TO RELATED APPLICATIONS

This application claims the benefit of U.S. Provisional Application No. 62/758,126, filed Nov. 9, 2019, the entire disclosure of which is incorporated herein by reference in its entirety.

BACKGROUND

Ischemic injury is a leading cause of brain cell and tissue loss after stroke. Even if patients survive the ischemic event, expensive post-stroke medical care, rehabilitation, and physical and mental services are often required and patients may be left with devastating neurological deficits. Unfortunately, only limited medical interventions are currently available for the treatment of ischemic stroke, and no targeted neuroprotective treatments have been developed. The paucity of available treatments may be due to the acute nature of the pathogenesis and the previous research focus on blocking neuronal receptors against excitotoxicity Excitotoxicity and $Ca^{2+}$ overload stress are hallmarks of ischemic injuries such as stroke, ischemic myocardial infarction, and spinal cord injury. Most neuroprotective experimental treatments have focused on blocking glutamate receptors in neurons, but with no clinical benefit to date despite multiple trials over many decades.

Ischemia causes interruption of aerobic metabolism resulting in excess glutamate accumulation. High glutamate levels can overstimulate the neuronal glutamate receptors, leading to an influx of $Ca^{2+}$ and intracellular $Ca^{2+}$ overload. $Ca^{2+}$ overload plays a critical role in the pathogenesis of many cell death-associated diseases, such as stroke and heart attack, by hyperactivating poly(ADP-ribose) polymerase (PARP) and generating reactive oxygen species (ROS). The hyperactivation of PARP and spiked intracellular level of ROS are particularly cytotoxic, eventually leading to cell death, typically involving early necrosis and delayed apoptosis.

As a well-known key regulator in DNA damage responses (DDR), *Ataxia telangiectasia* and Rad3-related (ATR) kinase has been identified as a target for cancer therapies. However, prior to the instant disclosure, the relationship between ATR inhibition and neuroprotection has not been appreciated.

A need exists for effective neuroprotective therapies for the treatment of ischemic injuries, including stroke.

SUMMARY

The instant disclosure elucidates the role of ATR inhibition in neuroprotection, and more specifically, in (1) inhibiting non-proliferating resident cell death and (2) promoting proliferating immune cell death. Accordingly, provided herein are methods for the treatment of ischemic disease comprising administration of ATR inhibitors.

In one embodiment, a method of treating a subject suffering from an ischemic disease associated with $Ca^{2+}$ overload is provided, the method comprising administering to the subject an effective amount of an inhibitor of *Ataxia telangiectasia* and Rad3-related (ATR) kinase.

In another embodiment, a method of treating a subject suffering from acute ischemic stroke is provided, the method comprising administering to the subject an effective amount of berzosertib.

These and other objects, features, embodiments, and advantages will become apparent to those of ordinary skill in the art from a reading of the following detailed description and the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows ATR regulates cell death induced by $Ca^{2+}$ overload. (A) Dividing human neural SH-SY5Y cells cultured in Dulbecco's modified Eagle's medium (DMEM) supplemented with 10% fetal bovine serum were treated with glutamate (100 uM), quinolinic acid (QA, 1.0 mM) or ionomycin (10 uM) in the presence and absence of ATR inhibitor VE-822 (ATRi, 80 nM) for 2 hours before cell death was measured using LDH cytotoxicity assay (LDH toxicity kit, Promega) following the vendor's procedures. (B)-(C) human $ATR^{+/+}$ and $ATR^{flox/-}$ HCT116 cells and primary fibroblasts transfected with ATR siRNAs for 48 hrs were treated with ionomycin (10 uM) for the indicated periods before cell death was measured using standard trypan blue cytotoxicity assay. (D) Human myoblastic cells H9C2 were treated with VE-822, followed by a hypoxia/reperfusion assay in hypoxia/reperfusion incubator. (E) Terminally differentiated non-dividing SH-SY5Y cells were treated with glutamate (100 uM), QA (1.0 mM) and ionomycin (1.0 uM)±VE-822 before cell death was measured using cytotoxicity assay. (F) Primary cortical neurons from postnatal day 0-1 mice were maintained for 5 d before pretreatment for 1 hour with vehicle (0.1% DMSO) or VE-822 prior to incubation with 10 uM NMDA for 8 h. Note the numerous neurites in the ATRi-treated culture. (G) Live cells (rounded morphology-white arrowheads) were counted in 5 fields per well. (*, $p \le 0.01$).

FIG. 4 reports data supporting the finding that necrosis is the form of cell death induced by $Ca^{2+}$ overload in dividing cells. (A) $ATR^{+/+}$ and $ATR^{flox/-}$ cells were pre-treated with apoptosis inhibitor Z-VAD-FMK and then with ionomycin for cytotoxicity assay. (B)-(C) Morphologic analysis (phase-contrast microscopy) shows necrotic cells characterized by swelling (yellow arrows) and chromatin condensation (red arrows). As a control, camptothecin (CPT), a DNA double-strand break and typical apoptosis inducer, caused characteristic cell shrinkage and apoptotic bodies. (D) Western blot analysis indicates that activated (cleaved) caspases, indicative of apoptosis, were only present in cells treated with CPT, but not ionomycin. (E) A549 cells were transfected with control, ATR, or ATM siRNAs for 72 hrs, then treated with ionomycin for 4 hrs. Treated cells were either analyzed by Western blot or trypan blue staining for determination of cell death. (*, $p \le 0.01$).

FIG. 5 shows systemic ATR inhibitor treatment rescues neurons and function in mouse model of middle cerebral artery occlusion (MCAO). Adult mice injected i.p. with vehicle (A) over 3 d after a 30 min unilateral MCAO had larger infarcts (identified by GFAP+ astrocyte borders and more leukocyte (CD45) infiltration) in the brain at 7 d, than with ATR inhibitor (ATRi) VE-822 (B). (C) Quantification of infarct size as % of the contralateral side. Data are mean+SEM. N=4, 6, *p<0.05. (D) Use of the affected paw while rearing against a glass cylinder was increased to the near normal forelimb use index level (zero) with ATRi (n=7, 6). (E) The number of neurons identified by the area of NeuN staining in the infarct was increased by VE-822 treatment. (F) With vehicle the striatum was essentially devoid of neurons. (G) In VE-822 treated mice rescued neurons often appeared around blood vessels (identified by αSMA). (H) Grid walk analysis of VE-822-treated and mock-treated MCAO mice.

FIG. 6 shows ATR inhibitor causes death of macrophages/microglia and activated pericytes. (A) VE-822-treated mice had fewer CD45+ infiltrating leukocytes in the infarct at 7 d after MCAO, as shown by area measurements. N=4, 6, **p<0.01. (B) Only in ATR inhibitor-treated mice, a sub-set of CD45+ cells were double-labeled with TUNEL (white arrows), which identifies DNA breaks in dying cells. (C) These cells included CD68+ microglia/macrophages as shown by split cells in an adjacent section (yellow arrows). Note the perivascular CD68+ cell at the wall of a blood vessel (BV, pink arrow). (D) Cleaved caspase-3 was present in CD45+ and CD68+ cells (1 m confocal slice). (E) The number of TUNEL+ nuclei in the cortex and striatum was higher with the ATR inhibitor treatment. (F) Some of the CD45 cells expressed ATR. (G) After MCAO, ATR expression was induced in PDGFRβ+ pericytes in the infarct. Yellow arrows indicate the cells shown by confocal on the right. Bottom confocal: ATR is seen in a CD13+ pericyte around a microvessel. (H) In ATR inhibitor-treated mice, many pericytes, identified by Vitronectin (VTN), showed signs of necrotic cell death (I), including swelling and DNA fragmentation as shown by absent Hoechst staining (red arrows). Green arrows=healthy pericytes.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

An "effective amount," as used herein, refers to an amount of a substance (e.g., a therapeutic compound and/or composition) that elicits a desired biological response. In some embodiments, an effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of; reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain an effective amount when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be effective as described herein.

The term "administering," as used herein, refers to any route of administering an effective amount of a therapeutic agent. In embodiments, the administering includes, but is not limited to, intravenous, intraperitoneal, subcutaneous, intramuscular, oral, intracerebral, intraspinal, intrathecal, subarachnoid, epidural, periocular, intraocular administration, and the like. In a specific embodiment, the therapeutic agent is administered orally or intravenously.

As used herein, "ATR kinase inhibitor," "ATR inhibitor," and "ATRi" refer interchangeably to an agent that reduces the expression level and/or activity of ATR kinase protein and/or mRNA. Charrier, et al., *Discovery of Potent and Selective Inhibitors of Ataxia Telangiectasia and Rad3 Related (ATR) Protein Kinase as Potential Anticancer Agents*, J. Med. Chem. 54(7): 2320-30 (2011). Non-limiting examples of ATR inhibitors for use in the methods described herein include, but are not limited to, one or more of berzosertib, ceralasertib, VE-821, AZ20, M4344, BAY-1895344, and others as disclosed in Mei, et al., *Ataxia telangiectasia and Rad3-related inhibitors and cancer therapy: where we stand*, J. Hematol. Oncol. 12: 43 (2019). In a specific embodiment, the ATR inhibitor is selected from the group consisting of berzosertib, ceralasertib, VE-821, and AZ20. In a very specific embodiment, the ATR inhibitor is berzosertib.

Berzosertib, also known as VE-822, VX-970, or M6620, is a first-in-class selective ATR inhibitor developed by EMD Serono, having the following chemical structure:

Knegtel, et al., *Rational Design of 5-(4-(Isopropylsulfonyl)phenyl)-3-(3-(4-((methylamino)methyl)phenyl)isoxazol-5-yl)pyrazine-2-amine (VX-970, M6620): Optimization of Intra- and Intermolecular Polar Interactions of a New Ataxia Telangiectasia Mutated and Rad3-Related (ATR) Kinase Inhibitor*, J. Med. Chem. 62(11): 5547-61 (2019); U.S. 2014/0356456.

Ceralasertib, also known as AZD-6738, is a selective ATR inhibitor having the following chemical structure:

Ceralasertib is an orally available morpholino-pyrimidine-based inhibitor of ATR kinase developed by AstraZeneca. Ceralasertib selectively inhibits ATR activity by blocking downstream phosphorylation of the serine/threonine protein kinase CHK1. See Foote, et al., *Discovery and Characterization of AZD6738, a Potent Inhibitor of Ataxia Telangiectasia Mutated and RAD3 Related (ATR) Kinase with Application as an Anticancer Agent*, J. Med. Chem. 61(22): 9889-9907 (2018)

VE-821 is a selective ATR kinase inhibitor having the following chemical structure:

VE-821 selectively inhibits ATR activity by blocking downstream phosphorylation of the serine/threonine protein kinase CHK1.

AZ20 is a selective ATR inhibitor having the following chemical structure:

M4344, also known as VX-803, is a potent and selective orally available inhibitor of ATR, developed by Merck.

BAY-1895344 is an ATR inhibitor developed by Bayer, having the following chemical structure:

The terms "treat," "treatment," and "treating," as used herein, refer to a method of alleviating or abrogating a disease, disorder, and/or symptoms thereof in a subject, including a mammal. In certain embodiments, the subject is a human patient.

Figure 1:
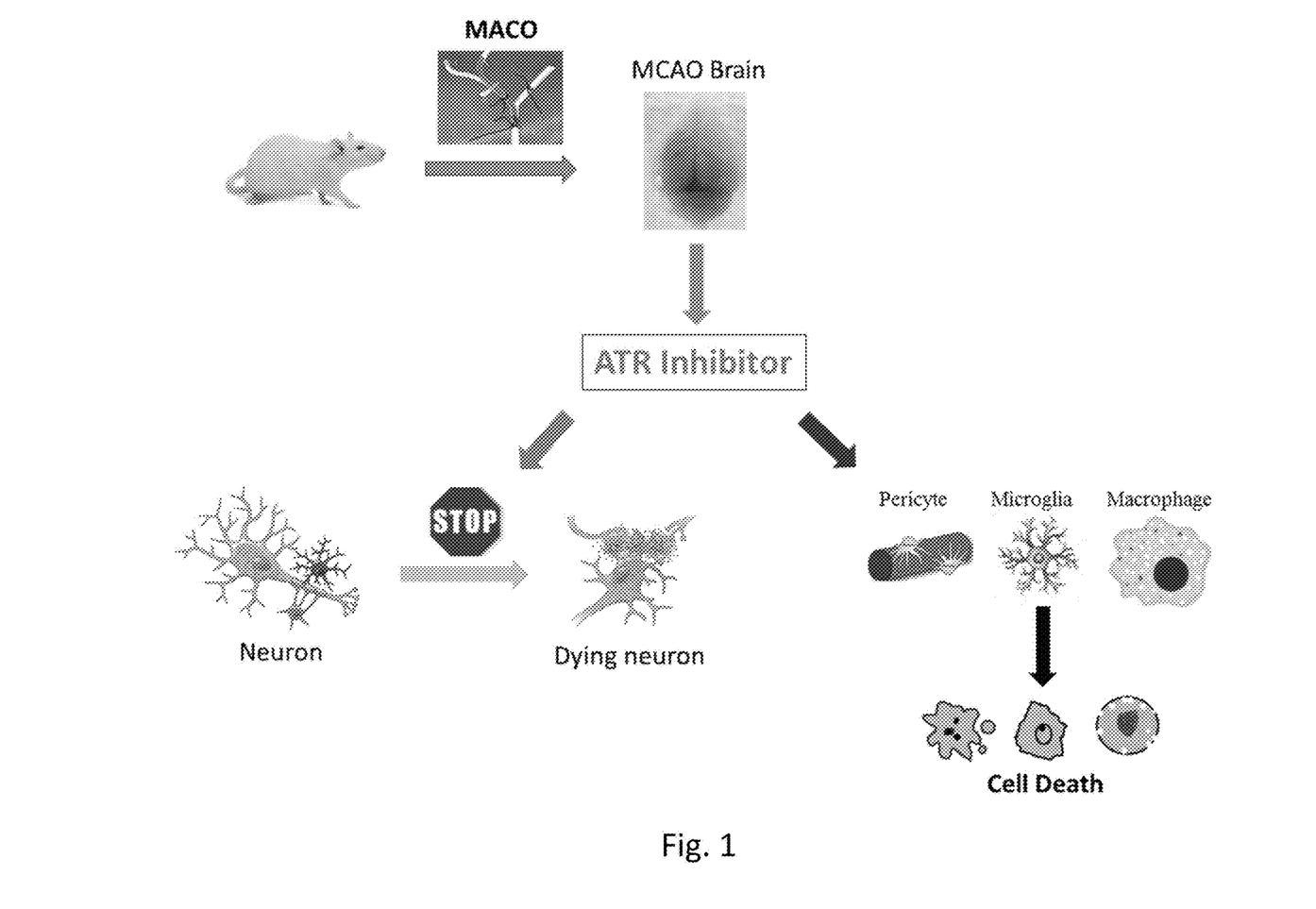
FIG. 1 illustrates the role of ATR inhibition in rescuing neurons and preventing neuron death while promoting death of damaging immune cells such as pericytes, microglia, and macrophages.

The present disclosure shows that ATR promotes $Ca^{2+}$ overload-induced death of terminally differentiated cells such as neurons, while protecting dividing cells (e.g., immune cells) from $Ca^{2+}$ overload-induced death. Inhibition of ATR suppresses $Ca^{2+}$ overload-induced death of terminally differentiated cells, while promoting dividing cell death induced by $Ca^{2+}$ overload. The present disclosure shows that systemic treatment with ATR kinase inhibitor VE-822, an anticancer drug currently in clinical trials, rescues neurons while killing pericytes, microglia, and infiltrating macrophages to suppress detrimental immune response in mice suffering middle cerebral artery occlusion (MCAO), a well-established stroke model. Further, systemic treatment with ATR kinase inhibitor VE-822 improves neurological conditions in mice post-MCAO (FIG. 1). The protection of mouse neurons or brain from stroke likely occurs at early period of time following MCAO.

The present inventors investigated the effects of ATR inhibition on survival of individual cell populations after stroke. Surprisingly, the present disclosure shows that inhibition of ATR kinase rescues one type of brain cell (terminally differentiated non-dividing neurons), while at the same time inducing death of detrimental cells (dividing immune cells). This finding underscores a creative new concept of synergistic effects induced by a single drug. The disclosed studies show that ATR plays a regulatory role not only in cellular DNA damage responses, but also in non-DNA damage stress ($Ca^{2+}$ overload) responses. The cell type-dependent effects of ATR inhibition have not been previously appreciated in the art.

Figure 9:
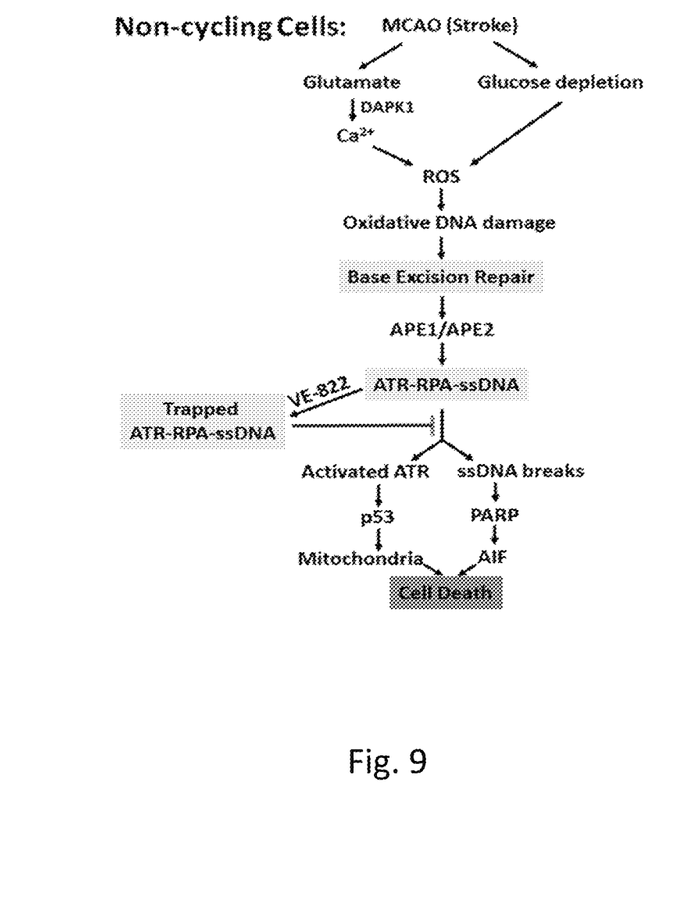
FIG. 9 is a schematic illustrating the role of ATR and inhibition by VE-822 in non-dividing cell death.
Figure 10:
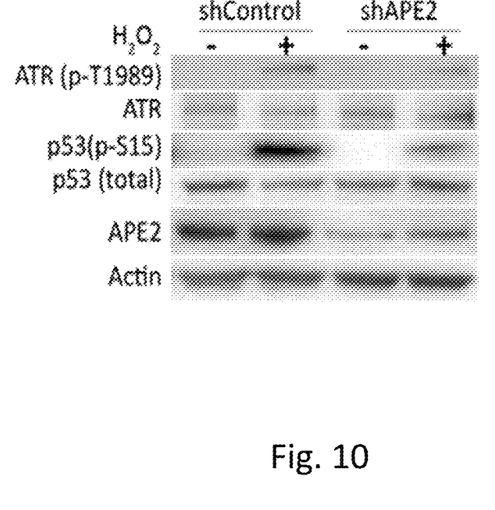
FIG. 10 depicts a Western blot demonstrating the effects of APE2 knockdown on ATR activation and p53 signaling in terminally differentiated SH-SY5Y cells.

Data reported herein indicate that ATR promotes death of non-dividing cells induced by $Ca^{2+}$ overload. While not desiring to be bound by theory, since $Ca^{2+}$ overload can eventually lead to ROS, oxidative DNA damage may be a major stress in terminally differentiated cells. In contrast, for differentiated and dividing cells in which PARP1 is highly expressed, cells experience a different type of stress related to cell death. In the case of neurons after stroke, ROS-induced oxidative DNA damage, rather than bulky DNA damage, is produced. Oxidative damage has little effect on transcription progression due to its relatively small modification to DNA, suggesting that the ATR effect on the $Ca^{2+}$ overload/ROS-induced cell death of neurons may occur by a different mechanism from that of dividing cells. Given that oxidative DNA damage is exclusively repaired by base excision repair (BER) system and ATR is involved in oxidative DNA damage-induced apoptosis in quiescent yeast, it is proposed that ATR can be activated by RPA-coated ssDNA generated during BER of excessive oxidative DNA damage in a replication-independent manner. Since apurinic/apyrimidinic (AP) endonuclease APE1/APE2 plays a key role in generating ssDNA during base excision repair, it is proposed that APE1/APE2 is required for the ATR activation (FIG. 9). After activation, ATR is released from RPA-ssDNA and then activates p53, a well-known pro-apoptotic protein, to induce cell death via transcriptional regulation and/or direct action at mitochondria. The data support requirement of APE2 for ATR activation and p53 signaling in non-dividing neuronal cells (FIG. 10). Also, ATR release may allow PARP1 activation by binding ssDNA breaks, triggering parthanatos (FIG. 9). By contrast, ATR inhibition traps ATR at ssDNA, suppressing p53-dependet apoptosis and preventing PARP1 from binding ssDNA breaks and activating parthanatos.

Accordingly, in one embodiment, a method of treating a subject suffering from an ischemic disease associated with $Ca^{2+}$ overload is provided, the method comprising administering to the subject an effective amount of an inhibitor of *Ataxia telangiectasia* and Rad3-related (ATR) kinase.

The cellular mechanisms underlying ischemic injury are discussed at length in Kalogeris, et al., *Cell Biology of Ischemia/Reperfusion Injury, Int. Rev. Cell Mol. Biol.* 298: 229-317 (2012), incorporated herein by reference in its entirety. Ischemic disorders involve interruption in blood supply to tissues or organs. In embodiments, ischemic diseases associated with $Ca^{2+}$ overload include, but are not limited to, myocardial ischemia, ischemic stroke, peripheral vascular disease, retinal ischemia, renal ischemia, and spinal cord injury. In a very specific embodiment, the ischemic disease associated with $Ca^{2+}$ overload is ischemic stroke, including acute ischemic stroke.

In embodiments, treatment with an ATR inhibitor comprises inhibiting non-proliferating resident cell death. In another embodiment, treatment with an ATR inhibitor comprises promoting proliferating immune cell death. In a specific embodiment, treatment with an ATR inhibitor simultaneously inhibits non-proliferating resident cell death and promotes proliferating immune cell death in a synergistic manner.

In embodiments, the methods disclosed herein further comprise administering to the subject an effective amount of a second therapeutic agent. The selection of second therapeutic agent will depend on the particular type of ischemic disease to be treated.

For the treatment of myocardial ischemia, second therapeutic agents may be selected from the group consisting of antiplatelet medications (such as aspirin, clopidogrel, ticagrelor, prasugrel, dipyridamole, ticlopidine, and eptifibatide), anticoagulant medications (such as tissue plasminogen activator (tPA), heparin, warfarin, rivaroxaban, dabigatran, apixaban, edoxaban, enoxaparin, and fondaparinux), anti-inflammatory agents, vasodilators (such as nitrates, ACE inhibitors, angiotensin receptor blockers, calcium channel blockers, sildenafil, magnesium-containing vasodilators, and the like), beta blockers, cholesterol-lowering agents, ranolazine, and combinations thereof.

For the treatment of ischemic stroke, second therapeutic agents may be selected from the group consisting of anti-platelet medications (such as aspirin, clopidogrel, ticagrelor, prasugrel, dipyridamole, ticlopidine, and eptifibatide), anticoagulant medications (such as tissue plasminogen activator (tPA), heparin, warfarin, rivaroxaban, dabigatran, apixaban, edoxaban, enoxaparin, and fondaparinux), anti-inflammatory agents, nimodipine, glutamate, NMDA receptor antagonists, ryanodine receptor antagonists, vasodilators (such as nitrates, ACE inhibitors, angiotensin receptor blockers, calcium channel blockers, sildenafil, magnesium-containing vasodilators, and the like), and combinations thereof. In a specific embodiment, the second therapeutic agent for the treatment of ischemic stroke is tissue plasminogen activator (tPA).

For the treatment of peripheral vascular disease, second therapeutic agent may be selected from the group consisting of antiplatelet medications (such as aspirin, clopidogrel, ticagrelor, prasugrel, dipyridamole, ticlopidine, and eptifibatide), anticoagulant medications (such as tissue plasminogen activator (tPA), heparin, warfarin, rivaroxaban, dabigatran, apixaban, edoxaban, enoxaparin, and fondaparinux), anti-inflammatory agents, cholesterol-lowering agents, cilostazol, pentoxifylline, anti-hypertension agents, vasodilators, and combinations thereof.

For the treatment of retinal ischemia, second therapeutic agent may be selected from the group consisting of antiplatelet medications (such as aspirin, clopidogrel, ticagrelor, prasugrel, dipyridamole, ticlopidine, and eptifibatide), anticoagulant medications (such as tissue plasminogen activator (tPA), heparin, warfarin, rivaroxaban, dabigatran, apixaban, edoxaban, enoxaparin, and fondaparinux), anti-inflammatory agents, anti-VEGF agents, intraocular pressure-lowering agents, urokinase, streptokinase, and combinations thereof. Additional therapeutic treatments include ocular massage.

For the treatment of renal ischemia, second therapeutic agent may be selected from the group consisting of antiplatelet medications (such as aspirin, clopidogrel, ticagrelor, prasugrel, dipyridamole, ticlopidine, and eptifibatide), anticoagulant medications (such as tissue plasminogen activator (tPA), anti-inflammatory agents, and combinations thereof.

For the treatment of spinal cord injury, second therapeutic agent may be selected from the group consisting of riluzole, anti-inflammatory agents (such as minocycline, methylprednisone, and the like), vasodilators, and combinations thereof.

In embodiments, the ATR kinase inhibitor and the second therapeutic agent are administered consecutively or concurrently. The ATR kinase inhibitor and the second therapeutic agent(s) may be administered in separate dosage forms or in the same unit dosage.

In embodiments, the methods further comprise therapeutic treatment, including mechanical thrombectomy.

In another embodiment, a method for treating a subject suffering from acute ischemic stroke is provided, the method comprising administering to the subject an effective amount of berzosertib. In embodiments, treatment with berzosertib comprises inhibiting non-proliferating resident cell death. In another embodiment, treatment with berzosertib comprises promoting proliferating immune cell death. In a specific embodiment, treatment with berzosertib simultaneously inhibits non-proliferating resident cell death and promotes proliferating immune cell death in a synergistic manner.

In embodiments, the method further comprises administering to the subject an effective amount of a second therapeutic agent selected from the group consisting of antiplatelet medications (such as aspirin, clopidogrel, ticagrelor, prasugrel, dipyridamole, ticlopidine, and eptifibatide), anticoagulant medications (such as tissue plasminogen activator (tPA), heparin, warfarin, rivaroxaban, dabigatran, apixaban, edoxaban, enoxaparin, and fondaparinux), anti-inflammatory agents, nimodipine, glutamate, NMDA receptor antagonists, ryanodine receptor antagonists, vasodilators, and combinations thereof. In a specific embodiment, the second therapeutic agent is selected from the group consisting of tissue plasminogen activator, nimodipine, glutamate, NMDA receptor antagonists, ryanodine receptor antagonists, vasodilators, and combinations thereof. In a more specific embodiment, the second therapeutic agent is tissue plasminogen activator. In embodiments, the berzosertib and the second therapeutic agent are administered consecutively or concurrently. Berzosertib and the second therapeutic agent(s) may be administered in separate dosage forms or in the same unit dosage. In embodiments, the methods further comprise therapeutic treatment, including mechanical thrombectomy.

EXAMPLES

The following examples are given by way of illustration and are in no way intended to limit the scope of the present invention.

Example 1. ATR Regulates Cell Death Induced by $Ca^{2+}$ Overload

Dividing human neural SH-SY5Y cells were treated with glutamate (100 uM), quinolinic acid (QA) (1.0 mM) or ionomycin (10 uM)±ATR inhibitor VE-822 (ATRi) for 2 hrs before cell death was measured using LDH cytotoxicity assay. Human $ATR^{+/+}$ and $ATR^{flox/-}$ HCT116 cells and primary fibroblasts±ATR siRNAs were treated with ionomycin (10 uM) for the indicated periods before cell death was measured using trypan blue cytotoxicity assay. Human myoblastic cells H9C2 were treated with VE-822, followed by a hypoxia/reperfusion assay. Terminally differentiated non-dividing SH-SY5Y cells were treated with glutamate (100 uM), QA (1.0 mM) and ionomycin (1.0 uM)±VE-822 before cell death was measured using cytotoxicity assay. Primary neuron cultures were performed as described before from the cortices of neonatal C57BL/6 mice (Kang, et al., Loss of neuron-astroglia interaction rapidly induces protective CNTF expression after stroke in mice, J. Neuroscience 32: 9277-87 (2012)). After 5 days, cells were treated for 1 h with vehicle (0.1% DMSO) or VE-822 prior to incubation with 10 uM NMDA for 8 h. Live cells (rounded morphology-white arrowheads) were counted in 5 fields per well. (*, $p \leq 0.01$).

Figure 2:
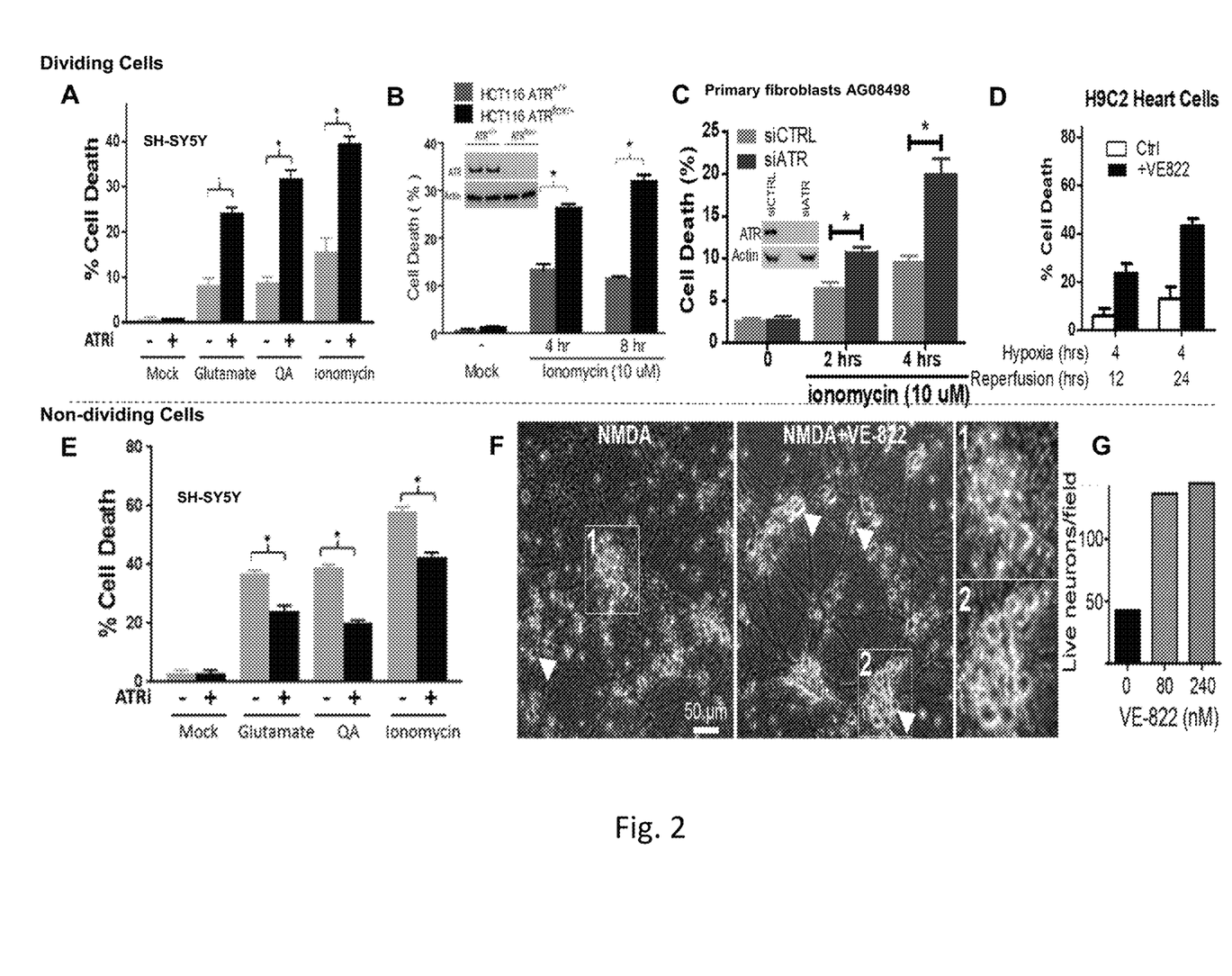

Results show that, in dividing cells, ATR kinase inhibitor (VE-822) dramatically increased cell death caused by cellular $Ca^{2+}$ overload inducers: glutamate, QA (quinolinic acid) and ionomycin (FIG. 2A). Increased death also occurred in dividing human NMDAR-deficient HCT116 cells after ATR deletion (HCT116-$ATR^{flox/-}$), primary fibroblasts±ATR siRNAs, and myoblastic cells±VE-822, all treated with ionomycin or in a hypoxia/reperfusion incubator (FIGS. 2B-2D). In sharp contrast, VE-822 rescued non-dividing differentiated SH-SY5Y cells under the same conditions (FIG. 2E). Primary cortical mouse neurons also were rescued from NMDA excitotoxicity by VE-822 (FIGS. 2F and 2G). Collectively, these data suggest that ATR is pro-survival for dividing cells, but anti-survival for non-dividing cells upon $Ca^{2+}$ overload.

Example 2. Apoptosis is Induced by $Ca^{2+}$ Overload in Non-Dividing Cells but is Reduced by ATR Inhibition Standard MTT cytotoxicity assay was carried out on terminally differentiated non-dividing SH-SY5Y cells treated with combinations of VE-822, Z-VAD-FMK, and glutamate. Cell differentiation: SH-SY5Y were grown to 60-70% confluency. Complete media was then replaced with 1% serum DMEM supplemented with freshly made all-trans retinoic acid dissolved in DMSO to a final in dish concentration of 10M. This media was changed every two days following the same composition until day ten. At day ten the media was replaced with 1% serum DMEM with no further supplementation. A washout period of two days was allowed before any experiments were performed.

Figure 3:
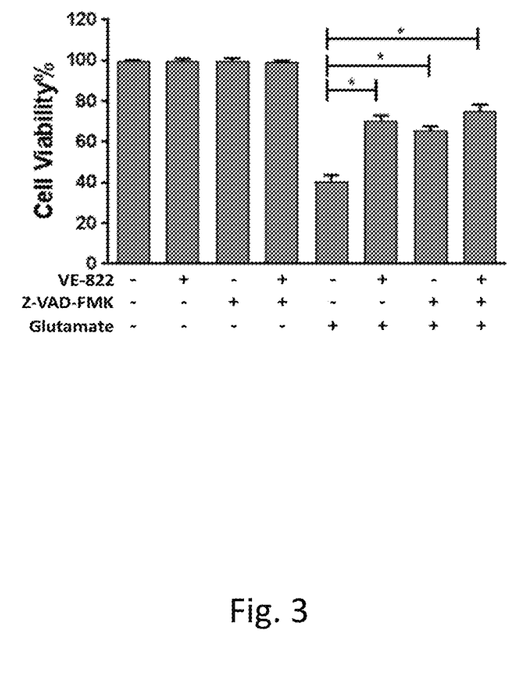
FIG. 3 depicts results of a cell viability assay (MTT) showing apoptosis is induced by $Ca^{2+}$ overload in terminally differentiated non-dividing SH-SY5Y cells but is reduced by ATR inhibition.

Results show that combining the apoptosis-specific inhibitor (Z-VAD-FMK) and ATR inhibition do not have additive effects in rescuing terminally differentiated SH-SY5Y cells from death, suggesting that ATR inhibition rescues non-dividing cells from apoptotic death (FIG. 3).

Example 3. Necrosis is Induced by $Ca^{2+}$ Overload in Dividing Cells

Figure 4:
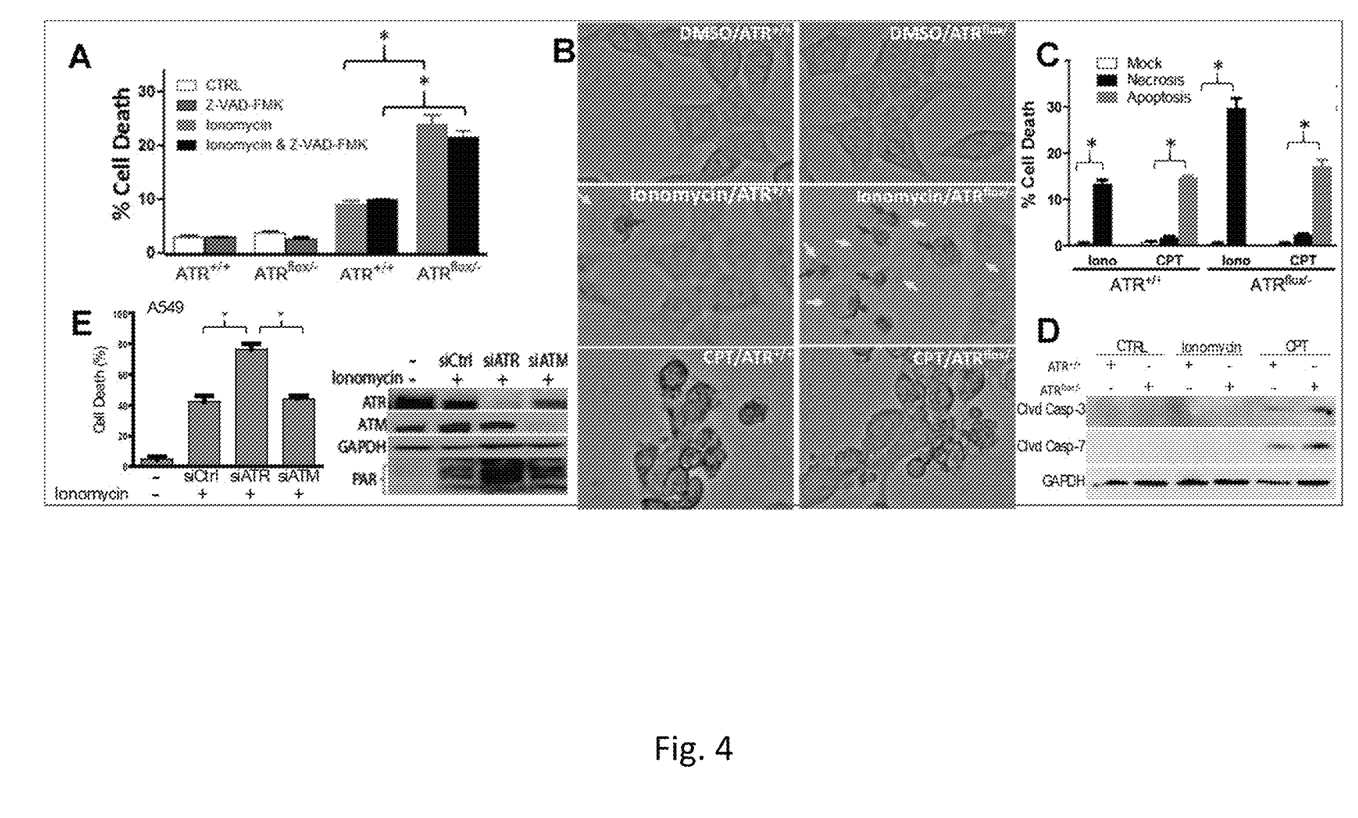

Cultured dividing $ATR^{+/+}$ and $ATR^{flox/-}$ HCT116 cells were pre-treated with apoptosis inhibitor Z-VAD-FMK and then with ionomycin, followed by trypan blue cytotoxicity assay (FIG. 4A). The same treated cells were also subjected to morphologic analysis (phase-contrast microscopy) (Vandenabeele et al., *Molecular mechanisms of necroptosis: an ordered cellular explosion, Nat. Rev. Mol. Cell Biol.* 11: 700-14 (2010); Krysko et al., *Apoptosis and necrosis: detection, discrimination and phagocytosis, Methods* 44(3): 205-21 (2008)), which showed necrotic cells characterized by swelling (yellow arrows) and chromatin condensation (red arrows) (FIGS. 4B and 4C). As a control, CPT, a DNA double-strand break and typical apoptosis inducer, caused characteristic cell shrinkage and apoptotic bodies. In FIG. 4D, Western blot analysis was carried out to show that activated (cleaved) caspases, a marker for apoptosis, were only found in cells treated with CPT, but not with ionomycin. FIG. 4E: Dividing A549 cells were transfected with control, ATR, or ATM siRNAs for 72 hrs, then treated with ionomycin for 4 hrs. Treated cells were either analyzed by Western blot or subjected to trypan blue staining for determination of cell death. (*, $p \leq 0.01$).

Results show that, in sharp contrast to non-dividing cells, pretreatment of dividing $ATR^{+/+}$ and HCT116-$ATR^{flox/-}$ cells with apoptosis inhibitor Z-VAD-FMK had no effect on cell death (FIG. 4A), indicating the death process is non-apoptotic. A cell morphology-based assay was used to compare cells treated with ionomycin vs. the apoptosis-inducer camptothecin (CPT) (FIG. 4B, C). Necrotic cell death characterized by chromatin condensation, an increasingly translucent cytoplasm, and cell swelling was induced by ionomycin. In contrast, CPT efficiently induced apoptosis as characterized by cell shrinkage/apoptotic bodies. The data show that ionomycin-induced $Ca^{2+}$ overload in cells caused necrosis while CPT induced apoptosis. Western blotting confirmed the absence of caspase activation in ionomycin-treated cells, which was obvious with CTP (FIG. 4D). The necrotic cell death induced by ionomycin in HCT116 and A549 cells and primary fibroblasts was confirmed by flow cytometric analysis of necrotic and apoptotic cells (data not shown). Finally, A549 cells transfected with the siRNAs against ATR, but not the siRNA against the closely related PIKK family member, ATM, showed significantly more cell death (FIG. 4E). Importantly, cell death depended on NAD+ depletion and was calpain-independent; and ionomycin or glutamate induced little/no DNA damage signaling and AIF activation in dividing SH-SY5Y cells as compared to controls for up to 8 hr, although DNA damage did occur at 24 hr (data not shown). Results indicate that early cell death is caused by necrosis, but not parthanatos.

Example 4. ATR Inhibition and Stroke Protection

Adult male C57BL/6 mice (10-12 weeks old; JAX Stock 000664, Jackson Labs) were anesthetized with Avertin and received a unilateral middle cerebral artery occlusion (MCAO) for 30 min as described (Kang et al., *Endogenous CNTF mediates stroke-induced adult CNS neurogenesis in mice, Neurobiology of Disease* 49: 68-78 (2013)). Reduced cortical blood flow was confirmed by Laser-Doppler Flowmetry and body temperature maintained during and after the MCAO. Two hours afterwards, ATR inhibitor VE-822 was injected i.p., and again at 24 and 48 h. One day before and at 3 and 7 days after MCAO, the mice were tested for impaired forepaw use in a glass cylinder test while rearing and the number of placement errors during grid walking. At 7 d mice were processed for histology of the brain as described (Kang et al., 2012, and Kang, et al., 2013), using various antibodies for cellular markers. Infarct size was determined by the area of lost cells in GFAP- and NeuN (neurons)-stained sections. Inflammatory cells were detected and identified with various antibodies and their death documented using an apoptosis detection kit and by nuclear staining.

Figure 5:
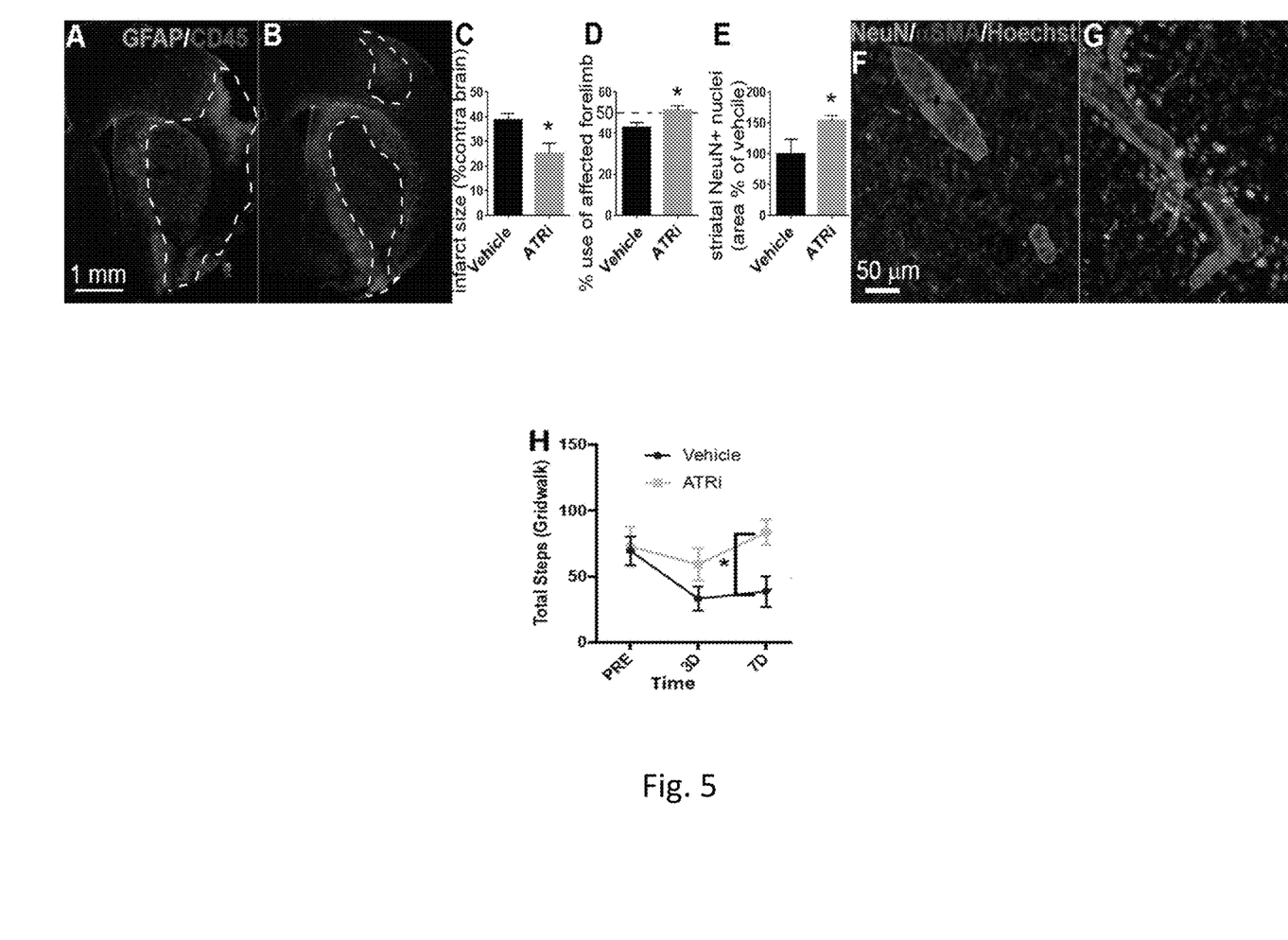
Figure 6:
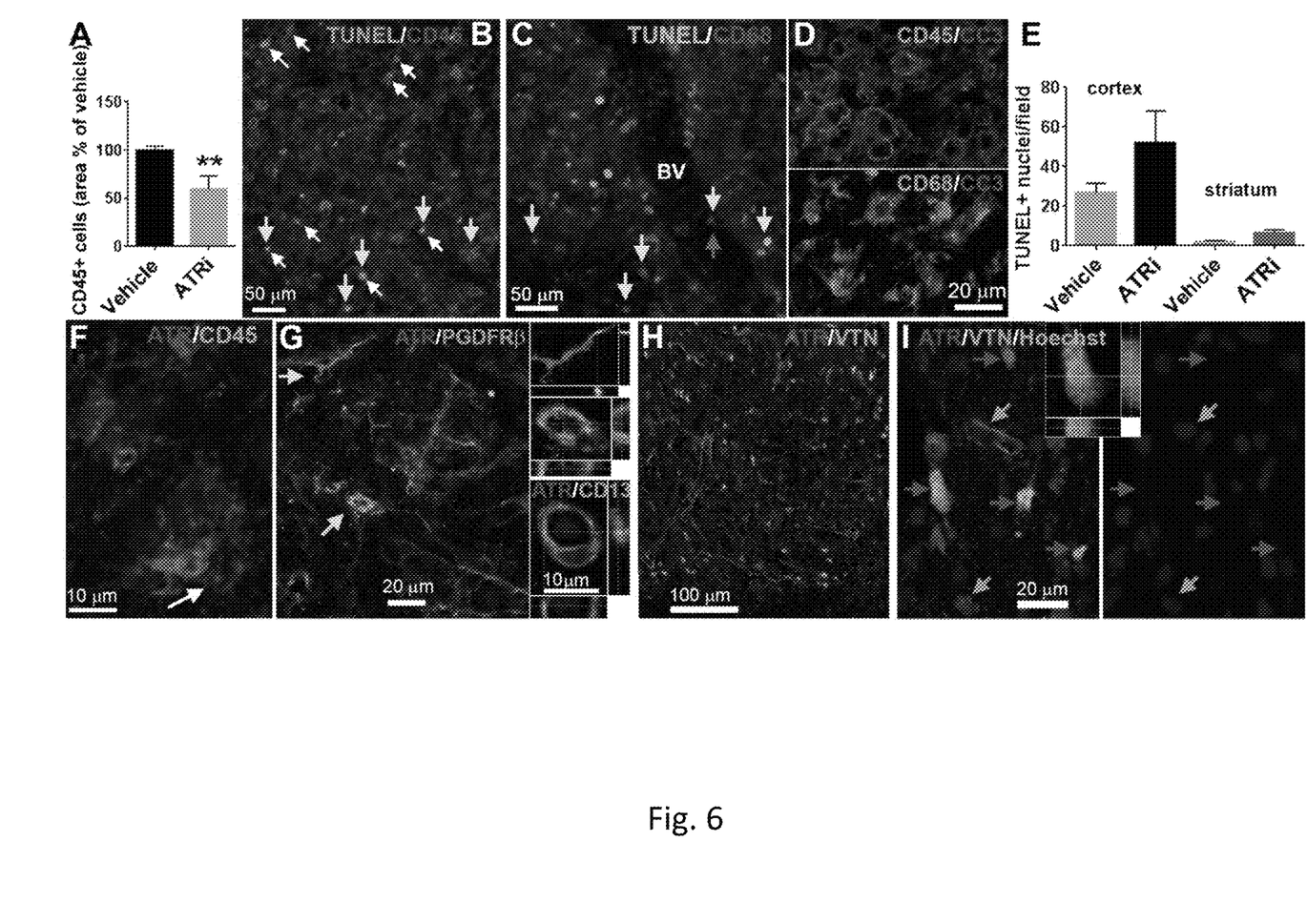

At 7 days after MCAO, those injected with VE-822 had smaller infarcts than those injected with vehicle (FIG. 5A-C). The reduction of blood flow measured by transcranial Doppler was the same between the two groups (not shown). The ATR inhibitor also improved neurological function as measured by affected paw use in a cylinder test (FIG. 5D) and grid-walking (FIG. 5H). Upon ATR inhibitor treatment, the number of neurons in the injury site was greater (FIG. 5E), with surviving neurons often seen around blood vessels (FIG. 5F, G), suggesting that the ATR inhibitor had entered the brain parenchyma In the same mice, those treated with the ATR inhibitor VE-822 had fewer CD45-positive leukocytes in the injury site (FIGS. 5A, B, 6A). A subset of leukocytes had undergone cell death, as shown by TUNEL staining (FIG. 6B). These dying leukocytes included macrophages or microglia (FIG. 6C) which also displayed cleaved caspase-3 staining (FIG. 6D). The number of TUNEL-positive cells in the injury site was increased in ATR inhibitor-treated mice (FIG. 6E). Some CD45+ cells expressed ATR (FIG. 6F). In the vehicle-treated mice, the MCAO induced de novo ATR expression in apparently healthy pericytes (identified by known markers and VTN), including those within the infarct (FIG. 6G). In sharp contrast, the ATR inhibitor caused a morphology consistent with necrosis, including retraction of the processes, swelling of the cell body and cellular disintegration (FIG. 6H, I). Results show ATR inhibition increases macrophage and pericyte death after stroke.

Example 5. $Ca^{2+}$ Overload Increases Cellular PARP Activity, Especially in ATR-Deficient Cells, and ATR Binding to PARP1

Since PARP hyperactivation is known to be the major cause of necrosis by $Ca^{2+}$ overload, the effects of ATR on PARsylation in dividing cells was investigated. A549 cells were treated with ionomycin (10 uM)+PARP inhibitor (3-ABA), followed by Western blot analysis of PAR formation. ATR+/+ and ATRflox/− cells were treated with ionomycin for the indicated periods. A549 cells were treated with ionomycin, followed by fractionation and ATR co-IP and Western blot analysis for PARP1 binding.

Figure 7:
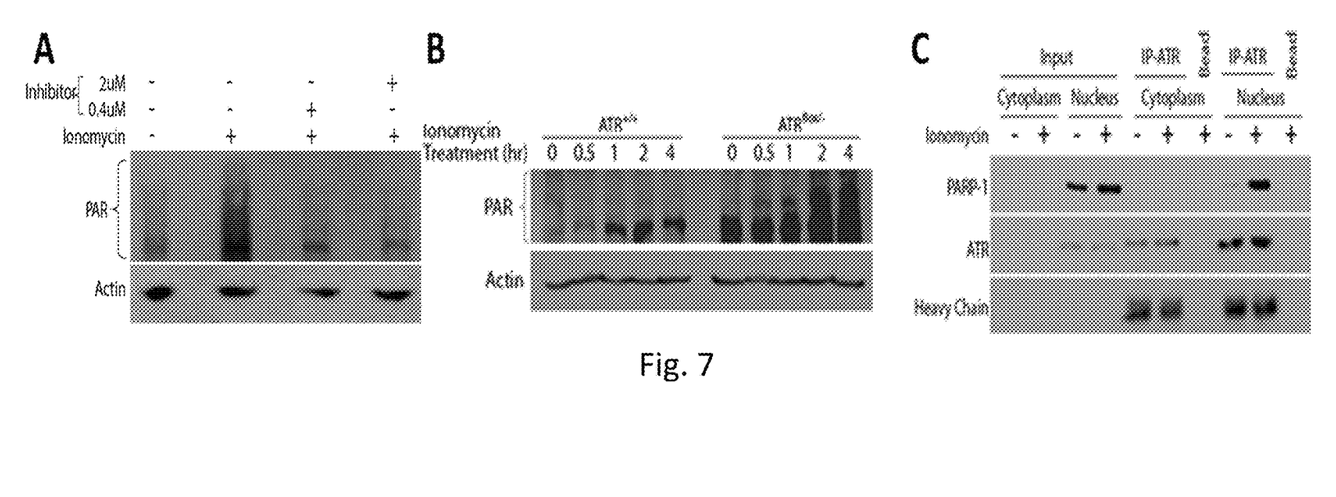
FIG. 7 shows $Ca^{2+}$ overload dramatically increases cellular PARP activity, especially in ATR-deficient cells, and ATR binding to PARP1. (A) Dividing A549 cells were treated with ionomycin (10 uM) in the presence of PARP inhibitor (3-ABA), followed by Western blot analysis of poly(ADP-ribose) (PAR) formation. (B) Dividing $ATR^{+/+}$ and $ATR^{flox/-}$ cells were treated with ionomycin for the indicated periods. (C) Dividing A549 cells were treated with ionomycin, followed by subcellular fractionation and co-immunoprecipitation with ATR antibody and Western blot analysis for PARP1 binding.

Results show that ionomycin increased PARP activity as measured by formation of PAR polymers, which was greatly reduced by a PARP inhibitor (FIG. 7A). Comparison between $ATR^{+/+}$ and $ATR^{flox/-}$ cells for PARsylation also indicated that PARP activity was dramatically higher in $ATR^{flox/-}$ cells versus in $ATR^{+/+}$ cells (FIG. 7B). Cells with siRNA knockdown of ATR generated the similar PARsylation results (FIG. 4E). Co-immunoprecipitation (co-IP) assays showed that ATR interacts with PARP1 in ionomycin-treated but not in control cells (FIG. 7C), indicating that ATR binds to PARP1 upon $Ca^{2+}$ overload.

Example 6. ATR Effects on PARP1 PARsylation in the Presence and Absence of $Ca^{2+}$ or DNA Damage In vitro PARsylation assay with $^{32}P$-labeled $NAD^+$ and purified PARP1 was performed in the presence and absence of purified ATR and/or $Ca^{2+}$ or activated oligos (mimicking DNA breaks). After reaction for 30 min, samples were analyzed by immunoblotting.

Figure 8:
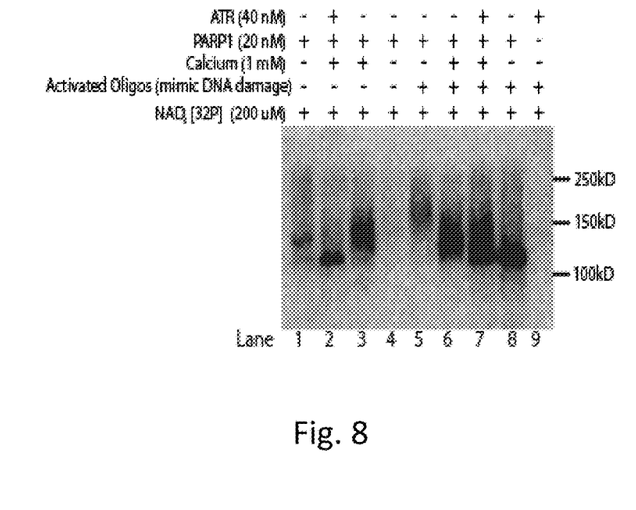
FIG. 8 shows ATR effects on PARP1 PARsylation in the presence and absence of $Ca^{2+}$ or DNA damage. In vitro PARsylation assay with $^{32}P$-labeled $NAD^+$ and purified PARP1 was performed in the presence and absence of purified ATR and/or $Ca^{2+}$ or activated oligos (mimicking DNA breaks). After reaction for 30 min, samples were analyzed by Western immunoblotting.

As shown in FIG. 8, ATR suppresses poly(ADP ribosyl) altion while allowing a smaller amount of likely mono(ADP ribosy)lation of PARP1 in the presence of $Ca^{2+}$ (lanes 2 vs. 3). By contrast, in the presence of damaged DNA, both mono and poly(ADP ribosyl) lations were significantly increased by ATR (lanes 5 vs. 7 and lanes 6 vs. 7). The opposite effects of ATR on PARsylation suggest that ATR regulates PARP1 activity very differently in the absence vs. presence of DNA damage.

Example 7. Effects of APE2 Knockdown on ATR Activation and p53 Signaling in Terminally Differentiated SH-SY5Y Cells Results (FIG. 10) show a Western blot analysis in which APE2 knockdown by shRNA has an effect on ATR activation and p53 signaling in terminally differentiated non-dividing SH-SY5Y cells. The data indicate that APE2 is required for ATR activation and p53 signaling in non-dividing neuronal cells as APE2 depletion by shRNA reduces p53 signaling.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A method of treating a subject suffering from an ischemic stroke, the method comprising administering to the subject an effective amount of an inhibitor of *Ataxia telangiectasia* and Rad3-related (ATR) kinase.

2. The method according to claim 1, wherein the inhibitor of ATR kinase is selected from the group consisting of berzosertib, ceralasertib, VE-821 (3-Amino-6-(4-(methyl-sulfonyl)phenyl)-N-phenylpyrazine-2-carboxamide), and AZ20 (4-[4-[(3R)-3-methyl-4-morpholinyl]-6-[1-(methyl sulfonyl)cyclopropyl]-2-pyrimidinyl]-1H-indole).

3. The method according to claim 2, wherein the inhibitor of ATR kinase is berzosertib.

4. The method according to claim 1, wherein the subject is a mammal.

5. The method according to claim 4, wherein the subject is a human.

6. The method according to claim 1, wherein treating comprises inhibiting non-proliferating resident cell death.

7. The method according to claim 1, wherein treating comprises promoting proliferating immune cell death.

8. The method according to claim 1, wherein the method further comprises administering to the subject an effective amount of second therapeutic agent.

9. The method according to claim 8, wherein the second therapeutic agent is selected from the group consisting of anti-platelet medications, anticoagulant medications, anti-inflammatory medications, vasodilators, and combinations thereof.

10. The method according to claim 9, wherein the second therapeutic agent is tissue plasminogen activator (tPA).

11. The method according to claim 8, wherein the inhibitor of ATR kinase and the second therapeutic agent are administered consecutively or concurrently.

12. The method according to claim 1, wherein administering is selected from the group consisting of intravenous, intraperitoneal, subcutaneous, intramuscular, oral, intracerebral, intraspinal, intrathecal, subarachnoid, epidural, periocular, and intraocular administration.

13. A method of treating a subject suffering from acute ischemic stroke, the method comprising administering to the subject an effective amount of berzosertib.

14. The method according to claim 13, wherein the subject is a mammal.

15. The method according to claim 14, wherein the subject is a human.

16. The method according to claim 13, wherein treating comprises inhibiting non-proliferating resident cell death.

17. The method according to claim 13, wherein treating comprises promoting proliferating immune cell death.

18. The method according to claim 13, wherein the method further comprises administering to the subject an effective amount of second therapeutic agent.

19. The method according to claim 18, wherein the second therapeutic agent is selected from the group consisting of antiplatelet medications, anticoagulant medications, anti-inflammatory agents, nimodipine, glutamate, NMDA receptor antagonists, ryanodine receptor antagonists, vasodilators, and combinations thereof.

20. The method according to claim 19, wherein the second therapeutic agent is tissue plasminogen activator (tPA).

21. The method according to claim 18, wherein the berzosertib and the second therapeutic agent are administered consecutively or concurrently.

22. The method according to claim 13, wherein administering is selected from the group consisting of intravenous, intraperitoneal, subcutaneous, intramuscular, oral, intracerebral, intraspinal, intrathecal, subarachnoid, epidural, periocular, and intraocular administration.

* * * * *